United States Patent [19]

Streeter

[11] Patent Number: 5,037,396
[45] Date of Patent: Aug. 6, 1991

[54] THERMOELECTRIC CHILLER AND AUTOMATIC SYRINGE

[75] Inventor: James M. Streeter, Highland, Utah

[73] Assignee: Becton, Dickinson and Company, Franklin Lakes, N.J.

[21] Appl. No.: 469,872

[22] Filed: Jan. 24, 1990

Related U.S. Application Data

[62] Division of Ser. No. 318,490, Mar. 2, 1989, Pat. No. 4,919,134.

[51] Int. Cl.$^5$ ............................................. A61M 1/00
[52] U.S. Cl. ............................. 604/152; 128/DIG. 1; 128/DIG. 12; 128/202.27; 604/208; 417/415
[58] Field of Search ............... 128/DIG. 1, DIG. 12, 128/202.27, 203.24; 604/65–67, 207–209, 131, 152; 417/360, 415

[56] References Cited

U.S. PATENT DOCUMENTS 3,698,288 10/1972 Sonabe ................................ 417/415
4,178,927 12/1979 Lundquist ..................... 128/DIG. 12
4,705,034 11/1987 Perkins ........................... 128/204.26
4,908,017 3/1990 Howson et al. ............... 128/DIG. 1

FOREIGN PATENT DOCUMENTS 0083870 7/1983 European Pat. Off. ............ 604/152
3639980 5/1988 Fed. Rep. of Germany ...... 604/131

*Primary Examiner*—Stephen C. Pellegrino
*Assistant Examiner*—Robin R. Longo
*Attorney, Agent, or Firm*—Aaron Passman

[57] ABSTRACT

An automatic syringe drive assembly and disposable heat exchanger cassette are used in combination to provide an improved thermodilution technique and apparatus. The automatic syringe drive assembly includes replaceable connecting rods on a slider crank mechanism which permit easy and accurate adjustment of the syringe injection volume. The drive assembly supports as insulated syringe for use in making the injection. The heat exchanger cassette includes a heat transfer plate and a thermoformed plastic labyrinth adhesively connected and used in combination with a thermoelectric chiller to provide a cold bolus of injectate.

7 Claims, 4 Drawing Sheets

THERMOELECTRIC CHILLER AND AUTOMATIC SYRINGE

This is a division of application Ser. No. 318,490, filed Mar. 2, 1989 now U.S. Pat. No. 4,919,134.

BACKGROUND OF THE INVENTION

This invention relates to a system for providing cold injectate to a thermodilution cardiac output measuring catheter. Thermodilution catheters have been used to determine cardiac output and these catheters are typically small diameter balloon types equipped with distal temperature sensing means and a lumen opening a short distance proximal to the temperature sensor for introduction of a low-temperature liquid injectate into the blood stream. The displacement of temperature resulting from the introduction of the low temperature injectate is sensed by the temperature sensing means, usually a thermistor. Such systems include a suitable supply of sterile injectate, usually 5% Dextrose in water or normal saline, and a multi-lumen catheter having at least one lumen with a thermistor in it, another for injectate, and yet another for a balloon. The injectate lumen has a proximal opening or port which is approximately 28 centimeters from the distal tip through which the injectate is infused. There is a thermistor distal therefrom and a balloon even more distal and finally a distal lumen.

The magnitude and duration of the temperature displacement over time can be used to compute the blood flow rate for a measure of a patient's cardiac output. U.S. Pat. No. 3,995,623 shows a typical thermodilution catheter. The blood flow rate is computed from the displacement of blood temperature according to the Stewart-Hamilton dilution equation for a thermal indicator as described in U.S. Pat. No. 3,987,788. As per that prior patent, numerical values are used for a computation constant, blood temperature, and injectate temperature. The computation constant is derived from the nature of the injectate, the volume of the injectate and a correction factor for the rise in temperature of the injectate as it passes through the lumen of the catheter to the injectate orifice.

Systems such as the Co-Set ™ from American Edwards Laboratories, Santa Ana, California require that the injectate be supplied by a syringe filled from a coil of tubing placed in a container filled with crushed ice. The ice covers the cooling coil of tubing and water is used to affect heat transfer between the tubing and the ice. The container is insulated styrofoam. Difficulties with thermodilution cardiac output monitoring include time wasted in loading the syringe, uncertainty of the syringe injectate temperature notwithstanding thermistors provided for that purpose, inconsistent techniques which are a consequence of the clinicians misuse or unfamiliarity with the apparatus and concern about air bubbles in the system as a consequence of the filling of the syringe and then injection with the syringe.

U.S. Pat. No. 3,293,868 issued Dec. 27, 1966 to F. A. Gonzalez for "Fluid Cooling Apparatus" describes a device having a flat plate with sinuous-shaped upstanding fins which form a channel for holding a length of flexible tubing through which blood or the like can be passed for heating or cooling. The plate is in contact with a number of spaced thermocouples which operate by virtue of the thermoelectric effect to heat or cool the plate depending upon the direction current is passed through the thermocouples. A rotary blower may be further used to remove heat from the fluid. The device is designed to be used in a generally horizontal position with the blood or other fluid being forced through the tubing by a pump or the like. The apparatus lacks an automatic injection system for easily and accurately delivered volumes of fluid and a simple disposable heat exchanger.

The Shah et al U.S. Pat. No. 4,532,414 shows an inline fluid warmer for heating parenteral fluids such as blood. The warmer includes an enclosure containing a heated plate having a sinuously-shaped groove configured to accept and hold the length of supply tubing in heat transfer relationship with the plate. Suitable temperature controls are provided to regulate the heat and keep the blood at the preferred level of heating. Good heat transfer in a disposable heat exchanger is not taught.

Inconsistencies in injectate temperature and variations in injection technique, such as injection speed or smoothness of the clinician can cause erroneous cardiac output measurements. These measurements could possibly result in inadvertent misdiagnosis and treatment which can be potentially fatal. Also, injection of air bubbles into the pulmonary vascular system is another potentially fatal situation due to the likelihood of pulmonary embolism.

Motor actuated syringes have been subject of numerous prior art patents, for example, U.S. Pat. Nos. 3,336,925; 3,156,236; 3,335,724; 2,896,621; 2,457,977; 3,313,291; 2,602,446; 2,498,672; and 3,584,623. However, none of these devices include an easily adjustable mechanism for accurately varying the amount of volume injected.

OBJECTS OF THE INVENTION

It is an object of the present invention to provide a system that has automatic injection of easily varied standard volumes of cold injectate.

It is a further object of the present invention to provide a thermoelectric cooling device for providing the chilled injectate.

It is still another object of the invention to have a simple, inexpensive disposable and efficient heat exchanger for use in combination with the thermoelectric cooler for the injectate.

SUMMARY OF THE DISCLOSURE

In order to overcome the problems of the prior devices and to teach a system which includes all of the necessary elements to provide a consistent, reliable, simple, and inexpensive arrangement which can be used without concern about variations in the skill level of the clinician, there is disclosed an automatically cooled injectate mechanism for use in combination with a cardiac output computer. The system includes an automatic drive device for an insulated syringe with a disposable cassette heat exchanger. The syringe and the cassette can be easily replaced in the basic system. Because of the disposable cassette and syringe, the basic mechanism of the system can be used repeatedly with different patients without concern of contamination or transfer of disease or infection.

More specifically, the disposable portions of the system are designed to be inexpensive and effective and easily used in combination with the basic mechanism of the system. The basic system disclosed has an automatic syringe driving mechanism which by merely changing a connecting rod will provide various stroke volumes without concern for sophisticated levels of adjustment. In addition to this, there is an injectate cooling device having a thermoelectric platen to which the disposable heat exchanger cassette can be easily attached for cooling injectate. The thermoelectric device is arranged to have intimate contact with the conductive portion of the disposable heat exchanger cassette such that cooling of injectate is uniformly, rapidly and efficiently accomplished. The temperature of the thermoelectrically chilled surface can be measured and used as input for the cardiac output computer whereby the injectate temperature is properly controlled.

This system is simple, light weight and portable in that it does not require a supply of ice or water. The basic mechanism is arranged to clamp the heat exchanger cassette conductive portion against the chilled surface of the thermoelectric cooler so that maximum surface contact is obtained and heat exchange takes place even though the heat exchanger cassette is disposable and easily replaced. The clamping mechanism is a door with a resilient nonconductive pad which acts not only as an insulator but as a clamping device to hold the cassette against the thermoelectrically chilled surface.

The automatic injectate syringe driving system includes a gear-reduced motor in combination with a slider crank mechanism, the connecting rod for which is easily interchanged to increase or decrease stroke and, therefore, the injectate volume. In the preferred embodiment various connecting rod lengths are provided and are selected to drive the syringe plunger in accordance with the stroke volume desired.

DETAILED DESCRIPTION OF THE DRAWINGS

Figure 1:
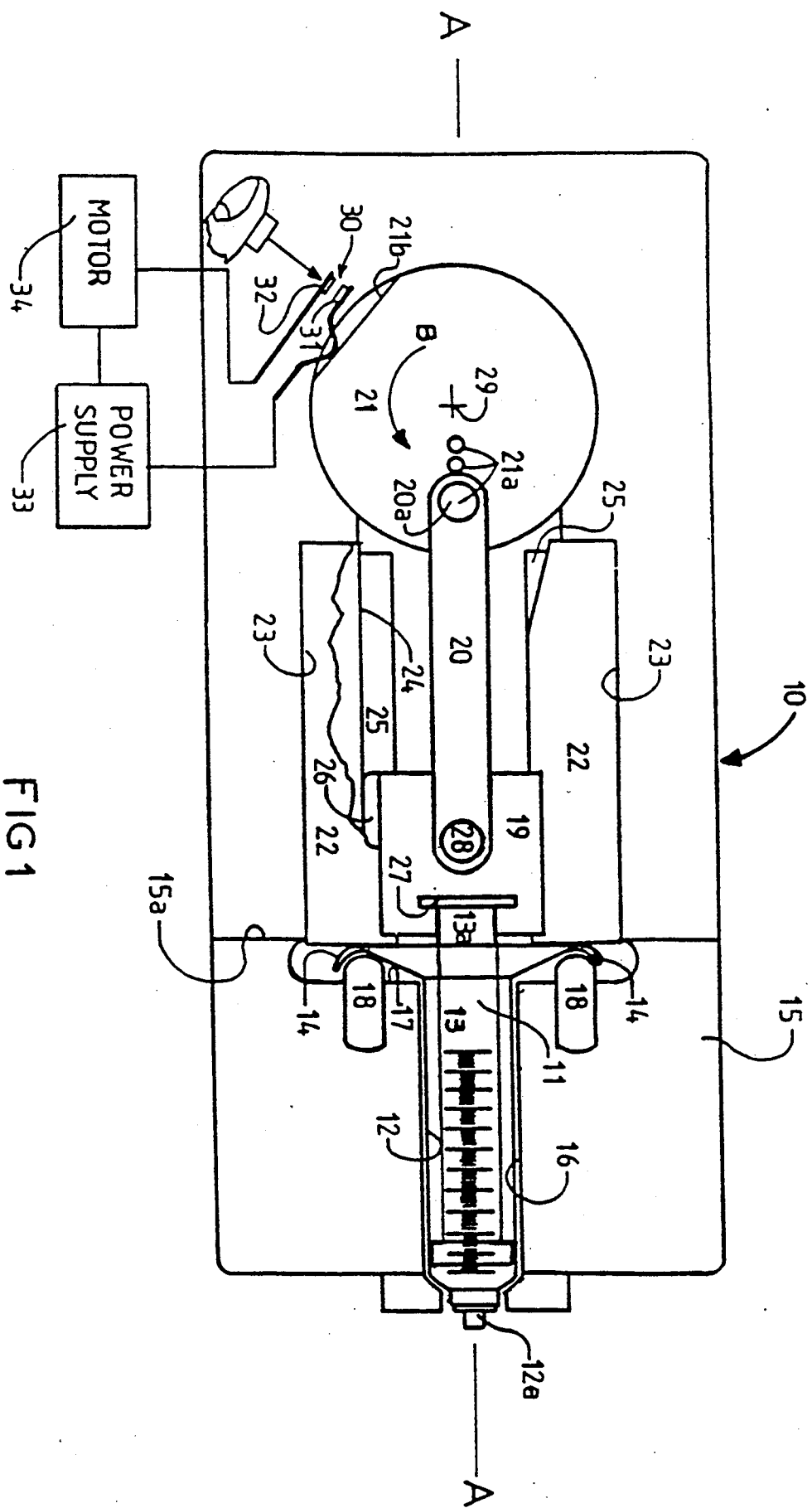
FIG. 1 is a plan view of the automatic injection drive mechanism composed of a slider crank mechanism for the preferred embodiment.

In FIG. 1 is an automatic syringe drive assembly 10 which supports an insulated syringe 11. The syringe 11 has a doubled wall insulated syringe barrel 12 and a plunger 13 which slides within the inner wall of barrel 12 of the syringe 11 to force fluids through the luer connector 12a located at the distal end of the insulated syringe 11. In the context of this description distal means toward the luer connection 12a and proximal means in the opposite direction. At the proximal end of the insulated syringe 11 are a pair of extending finger handles 14 which in normal or manual use are designed to fit the fingers of the syringe user. In the application of the automatic syringe drive assembly 10 the syringe 11 is held in a chassis 15 which is a heavy metal plate having specifically shaped openings to carry the components of the automatic syringe drive assembly 10. In particular, there is a syringe barrel recess 16 adapted and configured to support the insulated barrel 12 against side to side or axial movement.

At the proximal end of recess 16 in chassis 15 is a transverse recess 17 which extends outwardly from recess 16 to form a "T" shaped opening and to receive the handles 14. Adjustable tabs 18 are positioned parallel to recess 16 on each side thereof but spaced therefrom and each tab 18 extends into a part of handle recess 17 to bear against and hold the finger fitting portions of the handles 14. Adjustable tabs 18 can be moved toward and away from the handles 14 to cause each handle 18 to bear against its more proximal side of the recess 17.

In order to drive the plunger 13 there is a flat slider 19 which is driven by a connecting rod 20 rotated by a crank 21 at the connecting rod proximal end. The slider crank mechanism composed of the connecting rod 20, the crank 21 and the slider 19 convert the rotary motion of the crank 21 to reciprocating motion of the slider 19. The reciprocatory motion of slider 19 is controlled by guides 22 positioned within the chassis 15.

Specifically, the guides 22 have a groove arrangement for controlling the motion of a tongue on each side of slider 19. The particular components of the tongue and groove consist of chassis mounting channels 23 located parallel to slider 19 and carried within chassis 15. The guides 22 are received and supported in the operating plane of the insulated syringe 11, the slider 19, and the crank 21 whereby reciprocating motion of the slider 19 is in line with axis A-A of the plunger 13, see FIG. 1. Mounting channels 23 hold the guides 22 in position for supporting the slider 19. There is a groove 24 in each of the guides 22 which control the slider 19 for sliding reciprocatory motion in line with the axis A—A of plunger 13. Each groove 24 is formed within its respective guide 22 by a pair of extending flanges 25 designed to carry therebetween a tongue 26 extending transverse to and outwardly from each of the sides of piston 19. Consequently, as slider 19 reciprocates in response to forces transmitted through connecting rod 20 a tongue 26 on each side of slider 19 move within its respective groove 24. Motion of slider 19 is thus kept within the plane and axially relative to plunger 13.

In the distal end of slider 19 is a "T" shaped opening 27 which receives the end 13a of the plunger 13 to permit movement of the plunger 13 in the distal and proximal directions due to reciprocation of slider 19. At the proximal end of slider 19 is pin 28 which operates in a conventional fashion to allow pivotal motion between the distal end of the connecting rod 20 and the slider 19.

Crank 21 is supported by a shaft in a known manner for rotation about the crank center 29 in the direction shown by arrow B in FIG. 1. Chassis 15 is stepped at wall 15a to provide clearance for moving parts, 19, 20 and 21. The motor is shown schematically in FIG. 1 but is actually located beneath the chassis 15 to drive crank 21 about its center 29. Crank 21 has a series of threaded holes 21a positioned along a radius which are used in cooperation with connecting rods of varying length. Longer connecting rods 20 in combination with the arrangement shown in FIG. 1 will provide a shorter plunger stroke. A replaceable pin 20a connects the proximal end of connecting rod 20 to the crank 21. Pin 20a is in the nature of a shouldered threaded fastener that can easily be unscrewed from the hole 21a allowing replacement of the connecting rod 20 with another rod having a different length as shown in FIG. 1 in phantom lines. The distal end of connecting rod 20 is designed to slip over the pin 28. Since the motion of slider 19 is kept in the plane of reciprocation by the tongue and groove arrangement, no unseating forces are incurred at the connection of pin 28.

Crank 21 also includes a cam flat 21b which is used to control the starting and stopping point for the syringe drive assembly 10. Shown schematically is a switch 30 having a cam movable contact 31 which is responsive to cam flat 21b and a manually movable contact 32 such that switch 30 is normally closed except when movable contact 31 is against cam flat 21b. When against the cam flat 21b the switch 30 is opened and the circuit for the automatic syringe drive assembly 10 is disconnected. The manually operated contact 32 can be used to close switch 30 and start the automatic syringe drive 10. The operating circuit includes a power supply 33, one leg of which is connected to contact 32 and the other leg is connected to a motor 34 (shown schematically in FIG. 1). The other input for motor 34 is connected to the movable contact 31. When the crank 21 is in the position of FIG. 1 and the cam flat 21b has permitted moving contact 31 to break its connection from manually operated contact 32 and the motor 34 is disconnected from the power supply 33. Consequently, switch 30 can be overridden to activate the automatic syringe drive assembly 10. Switch 30 is designed to control the position at which the slider 19 begins and ends its reciprocatory motion. With this arrangement the mechanism of the automatic syringe drive assembly 10 can be manually started and automatically stopped for use in providing one complete stroke. The plunger 13 begins and ends each stroke at the same point, i.e. the most distal end of its travel with the particular length of connecting rod used. The stroke of plunger 13 is easily and accurately changed. The volume of injection is entirely automatic and easily and accurately set.

Figure 2:
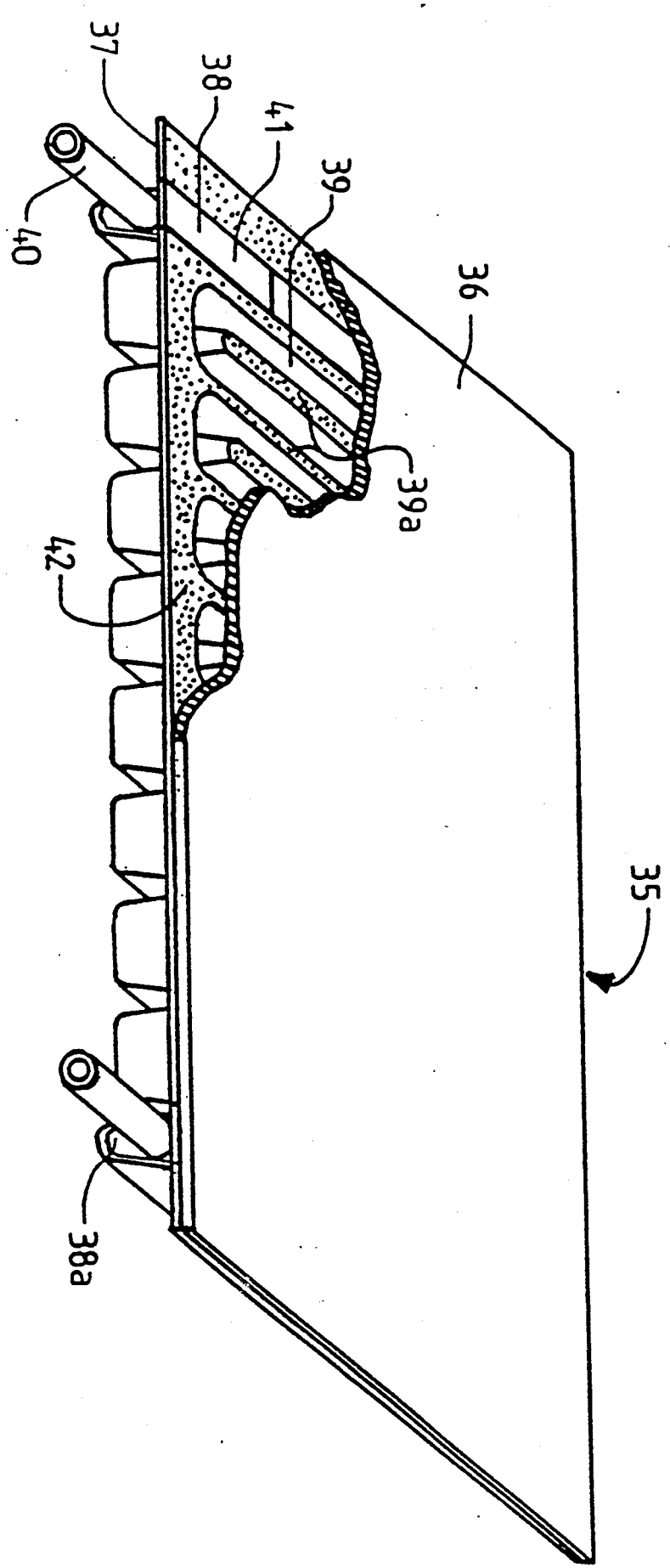
FIG. 2 is a perspective view partially cut away of the disposable heat exchanger cassette of the preferred embodiment.

FIG. 2 shows the perspective view of a heat exchanger cassette 35 used in connection with the automatic syringe drive assembly 10. The heat exchanger cassette 35 consists of a conductive plate 36 formed of stainless steel sheet being 0.010 inches thick and measuring approximately 2.75 inches by 4.375 inches. These dimensions can be varied for the particular application and the stainless steel is a suitable grade and finish for medical use. Plate 36 is adhesively connected to a thermoformed plastic labyrinth 37 which has repetitive S-shaped convolutions. At the ends of the labyrinth 37 are specifically shaped connectors 38 arranged to terminate the open ends of the labyrinth 37. The labyrinth 37 consists of a channel 39 which is U-shaped in cross-section and forms a circuitous path by extending back and forth across beneath the plate 36 to form parallel passageways having a hair pin turn at each end. The open ends of channel 39 are filled with connectors 38 which convert the generally U-shaped channel cross-section to a circular cross-section extending male tubing extension 40. A U-shaped portion 38a on each connector 38 is adhesively sealed into an open end of channel 39 with an extended fitting portion 41. Through extended fitting portion 41 passes a passage (not specifically shown) carefully shaped to gently funnel the flow from the U-shaped channel 39 to the circular cross-section of the male luer tubing extension 40.

Between each U-shaped channel 39 there are flat pad-like areas 39a positioned to rest against one of the major surfaces of the conductive plate 36. Between the areas 39a and the plate 36 is placed hot melt adhesive 42 which seals the labyrinth 37 to the plate 36 forming a fluid tight circuitous conductive path through the U-shaped channel 39. In particular, at the ends of channel 39 are connectors 38 which permit fluid to flow from one side of the heat exchanger assembly 35 to the other. As will be explained in detail, fluid passing through the labyrinth 37 formed by channel 39 exchanges heat. The volume of fluid contained by the preferred heat exchanger 35 is at least three times the stroke volume of the automatic syringe drive 10. Heat exchanger 35 is effective because the conductive plate 36 is metal and the labyrinth 37 is plastic. The combination is easily constructed and efficient in operation. It is also low cost, and, therefore, disposable. An additional safety feature is the hot melt adhesive 42 which cannot be autoclaved. Sterilization must be by radiation or ethylene oxide gas.

Figure 3:
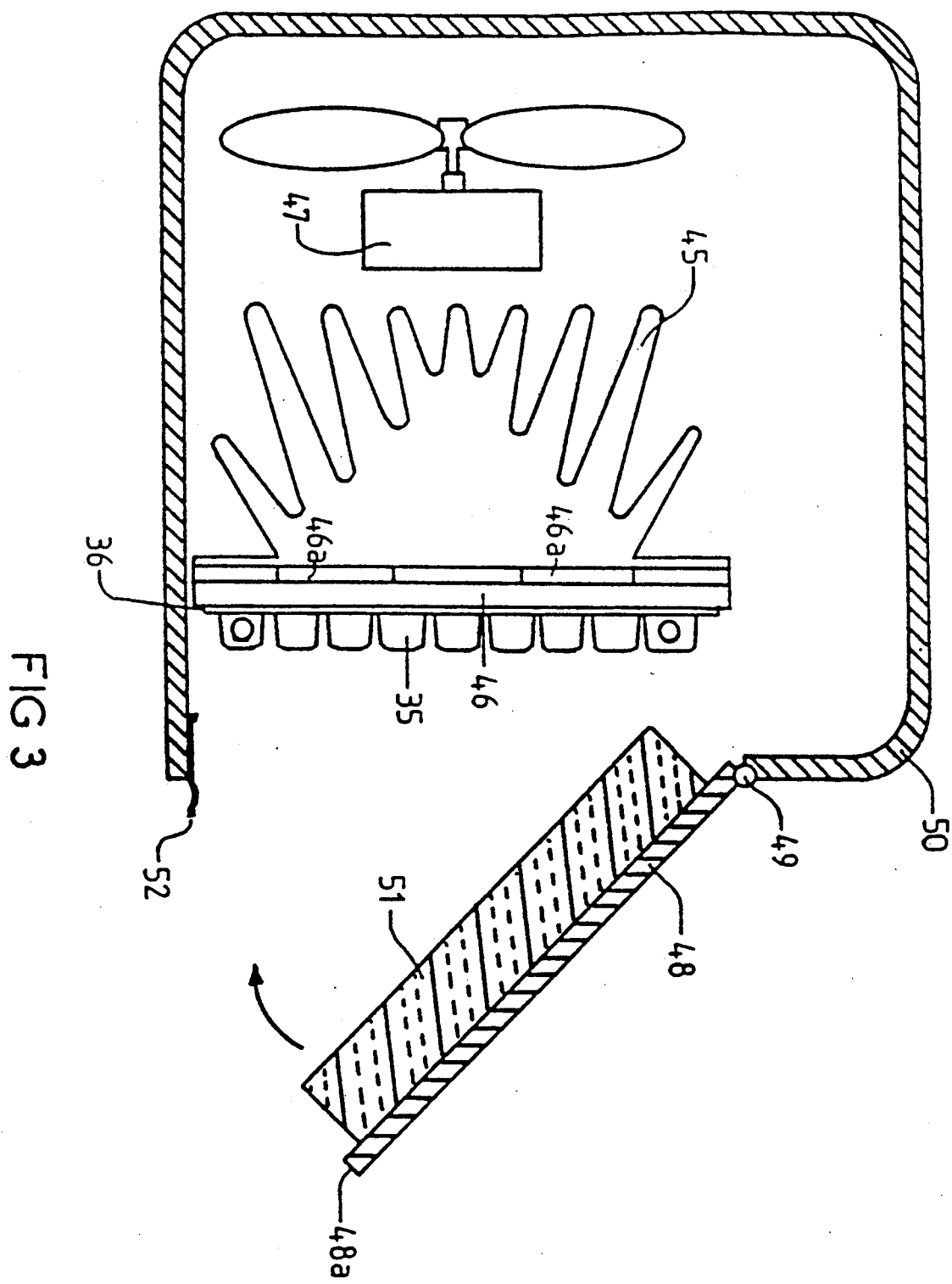
FIG. 3 is a top plan view with the housing in section showing the organization of the disposable heat exchanger cassette and the thermoelectric device used to change the temperature of the injectate bolus.

In operation the conductive plate 36 is held against the thermoelectric surface of a chiller whereby fluid passing through the labyrinth 37 is lowered in temperature to that of the conductive plate 36, see FIG. 3. In a preferred arrangement a thermoelectric chiller assembly 44, having a finned heat exchanger 45 with a series of junctions of dissimilar metals, causes the temperature of the finned heat exchanger 45 to change when a current is passed through the junctions. FIG. 3 is a top plan view of the arrangement for the thermoelectric chiller 44. More specifically, the way in which the disposable heat exchanger cassette 35 is brought to bear against the chilling surface of the thermoelectric chiller 44 is shown. The finned heat exchanger 45 is manufactured from an aluminum extrusion and is designed to support a chilled surface 46 which included the thermoelectric devices 46a that receive electrical current. Chilled surface 46 can include a thin coating of electrical insulation such as ceramic for safety. Depending upon the direction of electric current flow through devices 46a, the temperature will increase or decrease. In the preferred application temperature decrease is used to chill the surface 46. Opposite the cold surfaces of devices 46a are hot surfaces connected to finned heat exchangers 45 for heat removal. A fan assembly 47 is provided to move air across the finned heat exchanger 45 and thus lower the temperature of the heat exchanger 45 to ambient.

A door 48 carried upon a hinge 49 is supported upon a housing 50 for heat exchanger 45. The combination of door 48, hinge 49 and housing 50 permits easy replacement of the disposable heat exchanger cassette 35. The door 48 carries a resilient insulating foam pad 51 which is designed to bear against the labyrinth 37 of the heat exchanger cassette 35 and hold the conductive plate 36 against the chilled surface 46. It should be appreciated that the heat exchanger assembly 35 is in the nature of a disposable medical device so that with each procedure a new cassette can be used without complications or difficulty. This is important to prevent transmission of infection. The connectors 38 have male tubing extensions 40 which easily attach to the administration set on one end and the automatic syringe drive assembly 10 (at the luer connection 12a) on the other end. For that purpose there is a special tubing set which fits over extensions 40 and adapts to luer connections.

Figure 4:
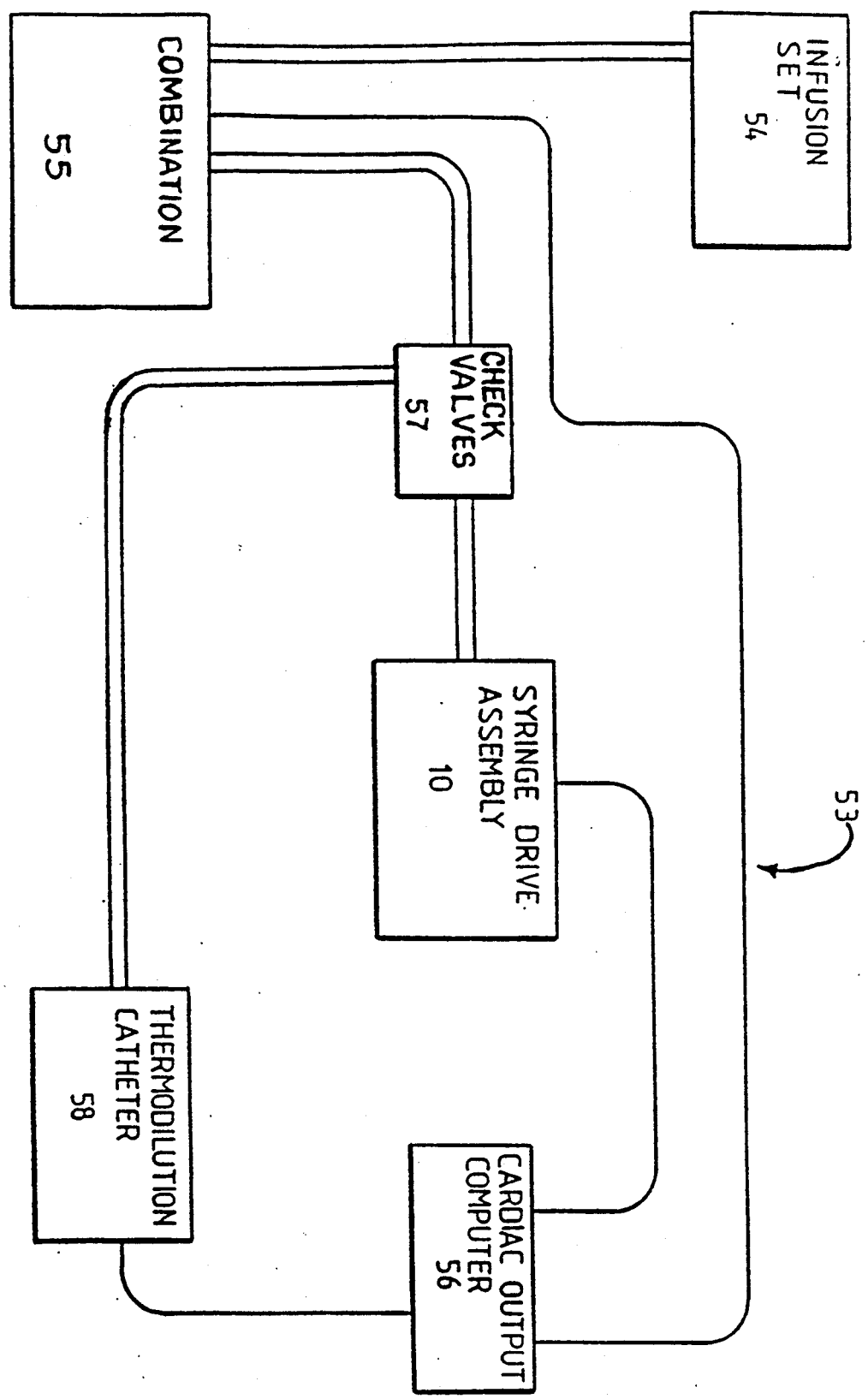
FIG. 4 is a block diagram showing the relationship of the components in the automatic injectate system of the present invention.

In order to hold the insulating foam pad 51 against the heat exchanger cassette 35, there is a housing latch 52 which cooperates with the edge of the door 48. In operation the chiller assembly 44 in combination with the cassette 35 (as shown in FIG. 3) function to replace the normal coil of flexible tubing and ice bath used in the American Edwards Co-set TM apparatus. That is to say that the arrangement schematically shown in FIG. 4 is known to medical practitioners except for the automatic syringe drive 10, the chiller 44 and disposable cassette 35 which are herein shown and describe. The coil and ice bath are replaced with the apparatus of FIG. 3. All of the plumbing including valves and connections are identical to that with which medical practitioners are familiar and that plumbing is arranged and used in accordance with conventional techniques. The apparatus of the present disclosure provides automatic repetitive and adjustable chilling of a bolus and is accurate, convenient and easy to use. In operation, the device of the present invention provides an accurately measured bolus at a preferred temperature, both of which are readily and automatically controlled in volume and temperature.

FIG. 4 is a block diagram of the automatic injection system 53 for purposes of explaining how the automatic syringe drive assembly 10, the disposable heat exchanger 35 and the thermoelectric chiller assembly 44 are used. The injectate is drawn from an infusion set 54 into the combination 55 which includes the thermoelectric chiller assembly 44 and disposable heat exchanger cassette 35. The operation of the syringe drive assembly 10 can be automatically controlled by a cardiac output computer 56 which is electrically connected to the automatic syringe drive assembly 10 and the combination 55 of disposable heat exchanger 35 and thermoelectric chiller assembly 44. Once the temperature of the injectate drawn from the infusion set 54 has reached the proper temperature, a signal is transmitted from the combination 55 to the computer 56 and in response thereto the automatic syringe drive assembly 10 is activated by means of its electrical connection to computer 56.

The flow of injectate as pumped by the syringe drive assembly 10 is controlled by check valves 57. The check valves 57 are arranged to permit fluid to first flow from the infusion set 54 to fill the combination 55 and then from there to thermodilution catheter 58. More specifically, the syringe drive assembly 10 is first filled from the infusion set 54 and then the syringe plunger 13 forces the injectate back through check valves 57 and into the thermodilution catheter 58. The check valves 57 are merely two one-way valves which permit flow from the infusion set 54 through the combination 55 (filling disposable heat exchanger cassette 35 and syringe) and then from the automatic syringe 10 and combination 55 to the thermodilution catheter 58.

The thermodilution catheter 58 is placed within the patient. In the patient end of the thermodilution catheter 58 is a thermistor which is electrically connected to the cardiac output computer 56 such that the temperature of that portion of the catheter can be monitored by the cardiac output computer.

To operate the combination 55 is electrically activated and filled with injectate by cycling syringe drive assembly 10. The automatic syringe drive assembly 10 is run through one cycle such that a volume of injectate is drawn from the infusion set 54 and purged through the system. During the purge the ambient injectate within the system is delivered to the patient. The volume of the disposable heat exchanger cassette 35 is at least three times that of one stroke of the syringe plunger 13. Therefore, the purge cycle is adequate to deliver all of the ambient injectate into the patient and leave the system completely filled with chilled injectate.

The system can be operated entirely automatically because of the electrical connection between the combination 55 and the cardiac output computer 56, as well as the electrical connection between the automatic syringe drive assembly 10 and the cardiac output computer 56. After the cardiac output computer 56 receives a signal from the thermistor of the thermodilution catheter 58 (i.e. the temperature of the patient end of the thermodilution catheter 58 has stabilized) the signal to inject a first chilled bolus is given by the cardiac output computer 56 to the automatic syringe drive 10.

As described in connection with FIG. 1, there is a manual override for switch 30 to activate the syringe drive 10. For fully automatic operation a shunt between the switched connections from the power supply 33 and the motor 34 will begin the operation of the automatic syringe 10. This shunt can be provided by the cardiac output computer 56 for a sufficient time to run the motor past the cam flat 21b and switch 30 will then complete the circuit and run the motor 34 for one complete cycle of the plunger 13.

Automatic plunger operation is qualified by the temperature of the chilled injectate which is measured in the chilled surface 46 of the thermoelectric chiller assembly. When that chilled surface 46 is at its operating temperature, the cardiac output computer 56 will start the cycle of the syringe drive assembly 10. The injection will be completed at the point where the movable contact 31 of switch 30 has again reached the cam flat 21b. The system is capable of manual operation. The thermoelectric chiller and cassette having reached operating temperature, a medical practitioner can manually start the cardiac output computer 56, and then the automatic syringe drive 10. The system when automatically or manually operated provides accurate and repeatable volumes of carefully cooled injectate.

While a preferred embodiment has been shown and describe in connection with the automatic injectate system for a bolus of a preselected volume, those skilled in the art will no doubt appreciate that changes and modifications can be made. The claims which follow seek to cover the broad concepts of the unique heat exchanger used to adjust the temperature of the bolus before injection and the simplified technique and mechanism designed to permit accurate and efficient change of injectate volumes in an automatic syringe drive mechanism.

What is claimed is:

1. An automatic syringe drive assembly for supporting an insulated syringe having a barrel with handles and plunger comprising;
    a chassis for supporting components to convert rotary motion to reciprocating motion;
    a motor supported by the chassis;
    a syringe barrel recess on the chassis located along an axis thereof, the syringe barrel recess for supporting the barrel against side to side and axial movement;
    a "T" shaped opening on the chassis proximal of the recess, the "T" shaped opening to receive the handles;
    a crank rotated by the motor, the crank having several mounting holes along a radius thereof, each mounting hole adapted to receive a replaceable pin;
    a linear guide on the chassis, the linear guide including a pair of parallel spaced apart channels along the axis, each of the channels having a groove;
    a pair of adjustable tabs extending into the "T" shaped opening to bear against and hold the handle of the syringe carried in the recess for maintaining the syringe barrel aligned axially relative to the parallel spaced apart channels;

a slider shaped to fit between the pair of parallel spaced apart channels for reciprocating linear motion therewithin, the slider connected to the plunger for moving the plunger with reciprocating linear motion relative to the syringe barrel, and a plurality of connecting rods of various lengths each connecting rod having a proximal end for connection to the crank for rotation about and association with the replaceable pin installed in one of the several mounting holes and a distal end for connection to the slider, each connecting rod capable when so disposed between the crank and the slider of setting the distance of linear motion of the plunger caused by the rotary motion of the crank as transferred to reciprocating motion of the slider.

2. The assembly of claim 1 wherein the replaceable pin cooperates with the proximal end of the connecting rod when the replaceable pin is secured in one of the several mounting holes by a threaded attachment.

3. The assembly of claim 1 wherein the proximal end and the distal end of each connecting rod means for removable connection to the crank and the slider so that connecting rods of different lengths can be substituted for one another to adjust the relative linear reciprocating motion to predetermined settings of the slider due to rotation of the crank and the mounting hole in which the replaceable pin is installed.

4. The system of claim 3 wherein the several mounting holes along a radius of the crank support the replaceable pin located on the crank at different distances along the radius thereof relative to the rotary center of the crank to adjust the stroke of the plunger in the barrel and the means for removable connection is slip fit about the distal end about the replaceable pin.

5. The assembly of claim 1 wherein connection of the slider to the plunger is through an opening in the plunger, the opening shaped to receive the end of the plunger and control the reciprocating motion of the plunger relative to the barrel.

6. The assembly of claim 1 wherein the slider has a pair of tongues extending therefrom, each tongue positioned to run in one of the grooves to maintain the slider in a plane defined by the rotation of the crank.

7. The system of claim 1 wherein the crank cooperates with a switched motor to start and cycle the plunger one revolution of the crank.

* * * * *